US007677247B2

(12) United States Patent
Turiello

(10) Patent No.: US 7,677,247 B2
(45) **Date of Patent: *Mar. 16, 2010**

(54) SAFETY SYSTEM AND METHOD OF AN UNDERGROUND MINE

(75) Inventor: Anthony J Turiello, Redwood City, CA (US)

(73) Assignee: Rescue Air Systems, Inc, San Carlos, CA (US)

( * ) Notice: Subject to any disclaimer, the term of this patent is extended or adjusted under 35 U.S.C. 154(b) by 512 days.

This patent is subject to a terminal disclaimer.

(21) Appl. No.: 11/505,525

(22) Filed: Aug. 16, 2006

(65) Prior Publication Data

US 2008/0041376 A1 Feb. 21, 2008

(51) Int. Cl.
*A61G 10/00* (2006.01)
*A61M 16/00* (2006.01)
*E04D 13/18* (2006.01)

(52) U.S. Cl. ........................... 128/205.26; 128/203.27; 128/204.18; 128/204.21; 52/173.3

(58) Field of Classification Search ............ 128/200.24, 128/201.24, 203.27, 204.18, 204.21, 205.26, 128/897, 898; 454/169–172; 52/2.1, 169.6, 52/302.1–302.7, 173.1–173.3, 2.11–2.26; 137/377, 382
See application file for complete search history.

(56) References Cited

U.S. PATENT DOCUMENTS

| | | | | |
|---|---|---|---|---|
| 2,299,763 | A * | 10/1942 | Ottenheimer | 312/119 |
| 2,299,793 | A * | 10/1942 | Cannaday et al. | 128/202.13 |
| 3,973,562 | A * | 8/1976 | Jansson | 128/205.12 |
| 3,995,626 | A * | 12/1976 | Pearce, Jr. | 128/205.24 |
| 4,712,594 | A * | 12/1987 | Schneider | 141/114 |
| 5,570,685 | A * | 11/1996 | Turiello | 128/202.13 |
| 5,979,440 | A * | 11/1999 | Honkonen et al. | 128/201.21 |
| 6,474,334 | B1 * | 11/2002 | Lemer | 128/204.18 |
| 6,701,923 | B2 * | 3/2004 | Cazenave et al. | 128/204.22 |
| 6,948,498 | B2 * | 9/2005 | Cazenave et al. | 128/204.22 |
| 7,055,780 | B2 * | 6/2006 | Phillips | 244/118.5 |
| 7,204,249 | B1 * | 4/2007 | Richey et al. | 128/204.18 |
| 7,255,104 | B2 * | 8/2007 | Phillips | 128/204.22 |
| 2006/0219842 | A1 * | 10/2006 | Shell et al. | 244/118.5 |

OTHER PUBLICATIONS

"New Firefighter Air System Makes High-Rise Fire-Fighting Safer; APS Stairwell Air-Replenishment System First of Its Kind in Arizona". Business Wire. Apr. 27, 2004.*
"1997 Phoenix Fire Code: Section 1008-Firefighter Air Systems Revision". Phoenix Fire Department. Jan. 9, 2004. pp. 1-6.*
"Standard Operating Procedure." Gorham Fire Department. Nov. 16, 1999. p. 1-3.*

* cited by examiner

*Primary Examiner*—Justine R Yu
*Assistant Examiner*—Annette F Dixon
(74) *Attorney, Agent, or Firm*—Raj Abhyanker LLP

(57) ABSTRACT

A breathable air safety system and method having at least one fill site is disclosed. In one aspect, a method of safety of a mine structure is disclosed. A prescribed pressure of an emergency support system is ensured to be within a threshold range of the prescribed pressure by including a valve of the emergency support system to prevent leakage of breathable air from the emergency support system. The prescribed pressure of the emergency support system is designated based on an authority agency that specifies a pressure rating of the breathable air apparatus. An air extraction process is expedited from the emergency support system by including a RIC (rapid interventions company/crew)/UAC (universal air connection) fitting to a fill panel to fill a breathable air apparatus.

7 Claims, 15 Drawing Sheets

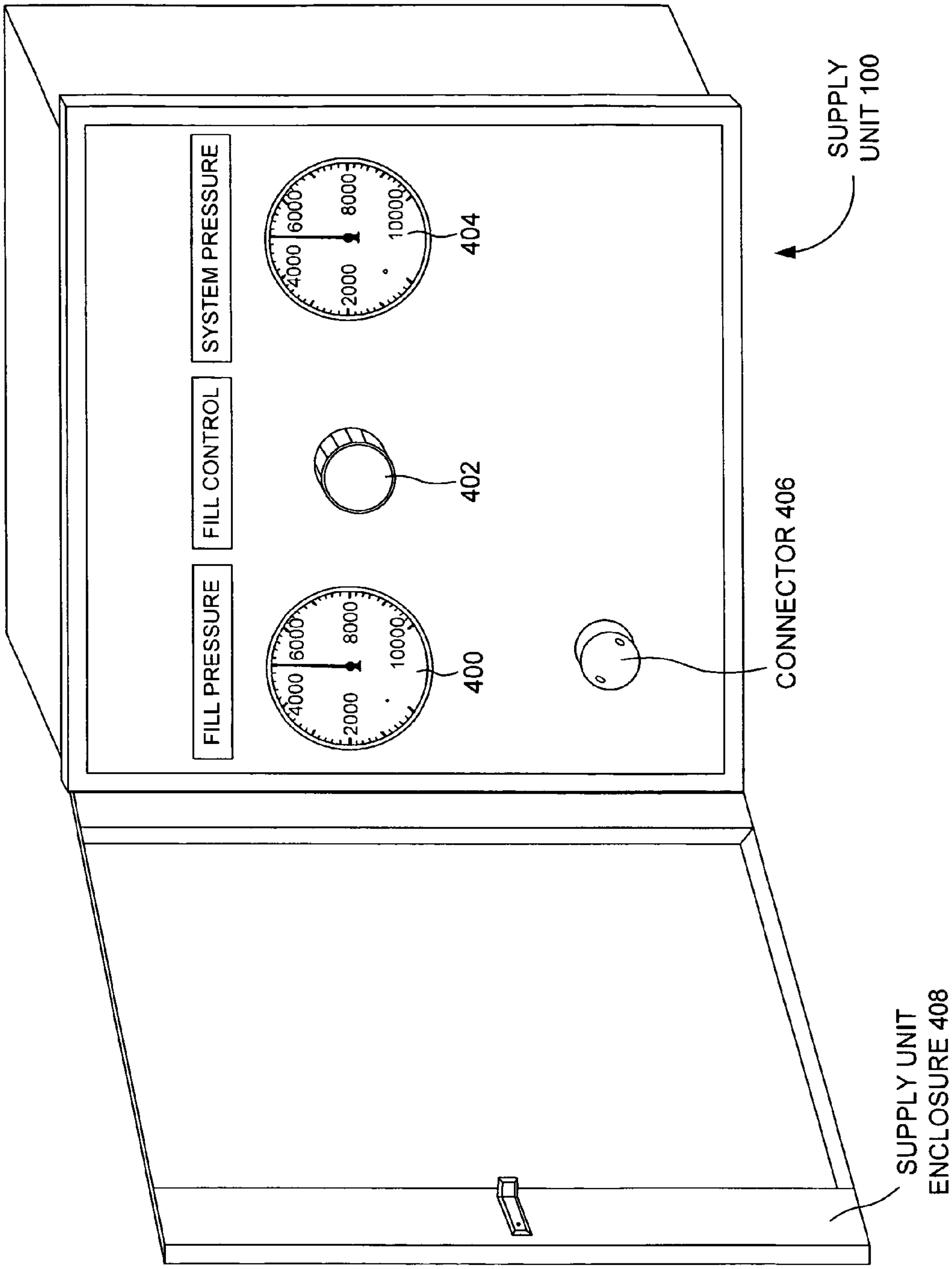
FIGURE 4A (FRONT VIEW)

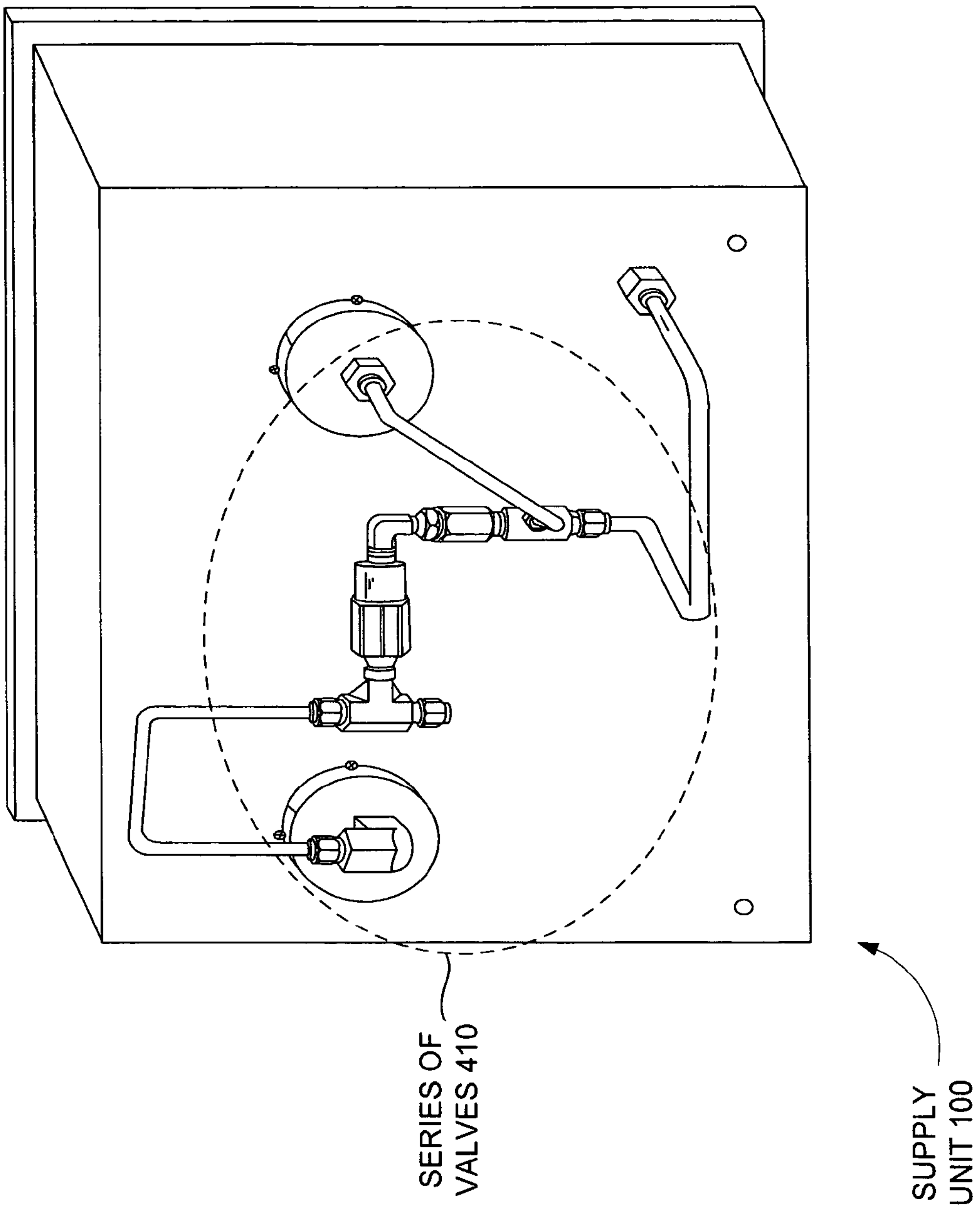
FIGURE 4B (REAR VIEW)

SAFETY SYSTEM AND METHOD OF AN UNDERGROUND MINE

FIELD OF TECHNOLOGY

This disclosure relates generally to the technical fields of safety systems and, in one example embodiment, to a safety system and method of a mine structure.

BACKGROUND

In a mine, providing and maintaining adequate safety may be of importance. For example, serious or fatal accidents occurring in underground mine in the United States over the years may have resulted from an inability to control the roof of the mine. For example, a fatal accident can occur from the falling of even one large rock from the roof of the mine.

In a case of an emergency situation of the mine, emergency personnel may be deployed on-site of the mine to alleviate the emergency situation through mitigating a source of hazard as well as rescuing stranded individuals from the mine. The emergency situation may include events such as a building fire, a chemical attack, terror attack, subway accident, underground mine collapse, and/or a biological agent attack.

In such situations, breathing air inside the mine may be hazardously affected (e.g., depleted, absorbed, and/or contaminated). In addition, flow of fresh air into the underground may be significantly hindered due to the mine having enclosed regions, lack of windows, and/or high concentration of contaminants. As a result, inhaling air in the mine may be extremely detrimental and may further result in death (e.g., within minutes). Furthermore, emergency work may often need to be performed from within the mine (e.g., due to a limitation of emergency equipment able to be transported on a ground level).

The emergency personnel's ability to alleviate the emergency in an efficient manner may be significantly limited by the lack of breathing air and/or the abundance of contaminated air. A survival rate of stranded civilians in the structure may substantially decreased due to a propagation of contaminated air throughout the mine placing a large number of innocent lives at significant risk.

As such, the emergency personnel may utilize a portable breathing air apparatus (e.g., self-contained breathing apparatus) as a source of breathing air during a rescue mission. However, the portable breathing air apparatus may be heavy (e.g., 20-30 pounds) and may only provide breathing air for a short while (e.g., approximately 15-30 minutes). In the emergency situation, the emergency personnel may need to walk and/or climb to a particular location within the mine to perform rescuing work due to inoperable transport systems (e.g., obstructed walkway, elevators, moving sidewalks, and/or escalators, etc.). As such, by the time the emergency personnel reaches the particular location, his/her portable breathing air apparatus may have already depleted and may require running back to the ground floor for a new portable breathing air apparatus. As a result, precious lives may be lost due to time being lost.

SUMMARY

A safety system and method of a mine structure are disclosed.

In one aspect, a safety system of a mine structure includes a supply unit of a mine structure to facilitate delivery of breathable air from a source of compressed air to an air distribution system of the mine structure, a valve to prevent leakage of the breathable air from the air distribution system potentially leading to loss of system pressure, a fill site interior to the mine structure to provide the breathable air to a breathable air apparatus at multiple locations of the mine structure, a distribution structure that is compatible with use with compressed air that facilitates dissemination of the breathable air of the source of compressed air to multiple locations of the mine structure.

The system may include a secure chamber of the fill station as a safety shield that confines a possible rupture of an over-pressurized breathable air apparatus within the secure chamber. The system my also include a secure chamber of the fill station as a safety shield that confines a possible rupture of an over-pressurized breathable air apparatus within the secure chamber. The system may also include an air storage sub-system to provide an additional supply of air to the mine structure in addition to the source of compressed air and an air storage tank of the air storage sub-system to provide storage of air that is dispersible to multiple locations of the mine structure. The air storage sub-system may also include a booster tank coupled to the air storage tank to store compressed air of a higher pressure than the compressed air that is stored in the air storage tank and a driving air source of the air storage sub-system to pneumatically drive a piston of a pressure booster to maintain a higher pressure of the air distribution system such that a breathable air apparatus is reliably filled. The system may also include an air monitoring system to automatically track and record any of impurities and contaminants in the breathable air of the air distribution system. The air monitoring system may also include an automatic shut down feature to suspend air dissemination to the mine structure in a case that any of impurity levels and contaminant levels exceeds a safety threshold. The system may also include a pressure monitoring system to continuously track and record the system pressure of the air distribution system. Further, any of a CGA connector and RIC (rapid interventions company/crew)/UAC (universal air connection) connector of the supply unit may be included to facilitate a connection with the source of compressed air through ensuring compatibility with the source of compressed air. The system may also include an isolation valve of the fill station to isolate a fill station from a remaining portion of the air distribution system.

The system may also include at least one of a fire rated material and a fire rated assembly to enclose the distribution structure such that the distribution structure has the ability to withstand elevated temperatures for a prescribed period of time. A selector valve that is accessible by an emergency personnel may be included to isolate the source of compressed air from the air storage sub-system such that the breathable air of the source of compressed air is directly deliverable to the air fill station through the piping distribution. In another aspect, a method includes ensuring that a prescribed pressure of an emergency support system maintains within a threshold range of the prescribed pressure by including a valve of the emergency support system to prevent leakage of breathable air from the emergency support system, safeguarding a filling process of a breathable air apparatus by enclosing the breathable air apparatus in a secure chamber of a fill site of the emergency support system of the mine structure to provide a safe placement to supply the breathable air to the breathable air apparatus, and providing a spare storage of breathable air through an air storage tank of a storage sub-system to store breathable air that is replenishable with a source of compressed air.

The method may also include preventing leakage of air from the emergency support system leading to a potential pressure loss of the emergency support system through utilizing a valve of any of the supply unit and the fill site and discontinuing transfer of breathable air from the source of compressed air to the emergency support system through utilizing a valve of the emergency support system. The method may also include automatically releasing breathable air from the emergency support system when the system pressure of the emergency support system exceeds the prescribed pressure through triggering a safety relief valve of any of the supply unit and the fill site, ensuring compatibility of the emergency support system and the source of compressed air of an authority agency through any of a CGA connector and a RIC (rapid interventions company/crew)/UAC (universal air connection) connector of the supply unit. The method may also include adjusting a fill pressure to ensure that the fill pressure of the source of compressed air does not exceed the prescribed pressure of the emergency support system through a pressure regulator of the supply unit. The method may also include monitoring any of the system pressure of the emergency support system and the fill pressure of the source of compressed air through the pressure gauge of the supply unit enclosure.

BRIEF DESCRIPTION OF THE DRAWINGS

Example embodiments are illustrated by way of example and not limitation in the figures of the accompanying drawings, in which like references indicate similar elements and in which:

FIG. 4A is a front view of a supply unit, according to one embodiment.

FIG. 4B is a rear view of a supply unit, according to one embodiment.

Figure 1:
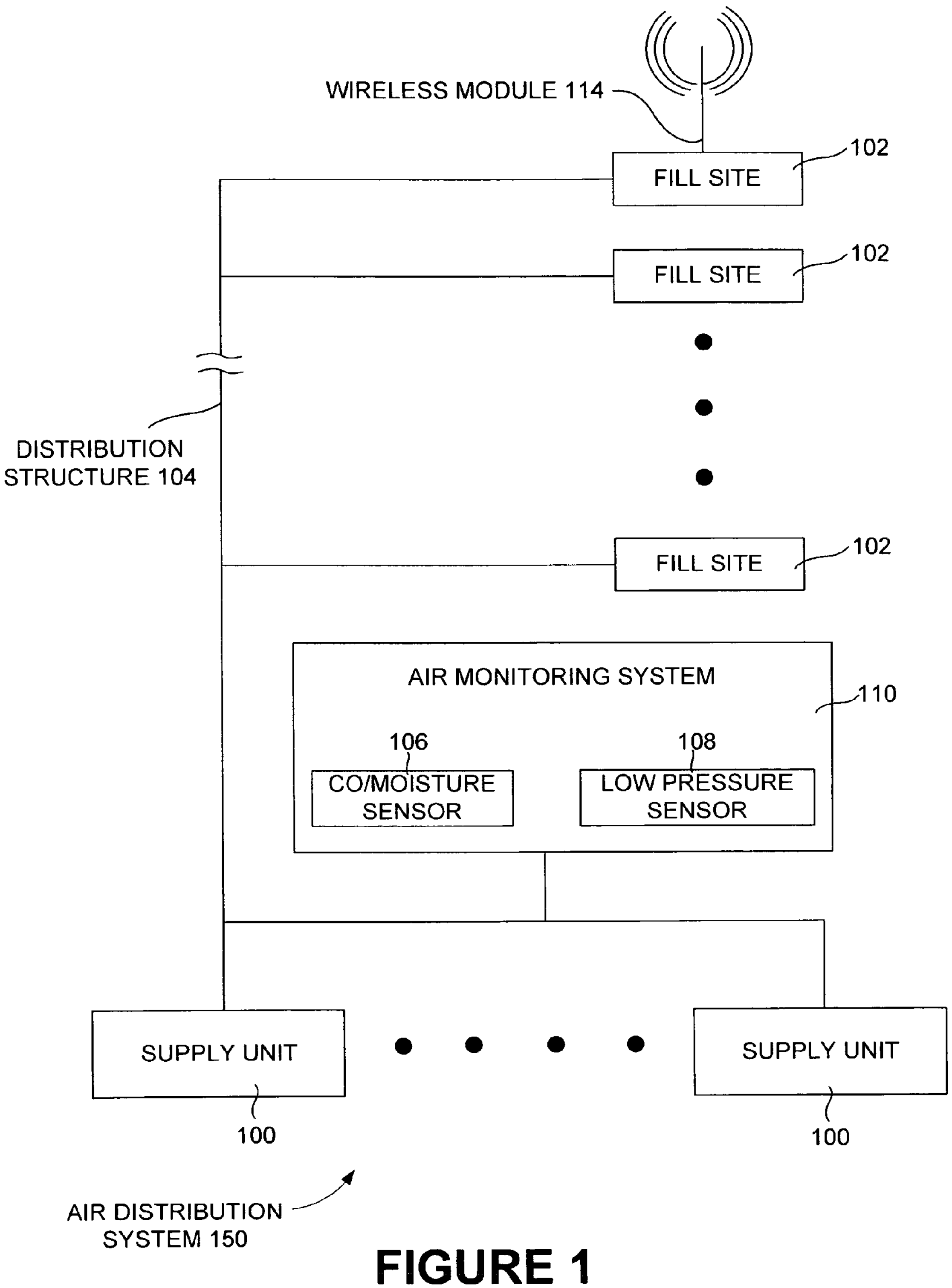
FIG. 1 is a diagram of an air distribution structure in a underground mine structure, according to one embodiment.

Other features of the present embodiments will be apparent from the accompanying drawings and from the detailed description that follows.

DETAILED DESCRIPTION

A safety system and method of a mine are disclosed. In the following description, for the purposes of explanation, numerous specific details are set forth in order to provide a thorough understanding of the various embodiments. It will be evident, however to one skilled in the art that the various embodiments may be practiced without these specific details.

Mine safety systems should be completely effective in order to provide safety for personnel working in the mines. The mine Safety and Health Administration (MSHA) is empowered by the United States government to enforce underground mine safety standards, including roof support standards, and to provide inspection of underground mine roof control plans and practices carried out in the mining industry. In order to comply with MSHA standards, underground mine must have a roof control plan in place, and such plan will invariably include provisions for what is known as "primary roof support." Primary roof support refers to abatement provisions designed to prevent a roof cave-in by effectively sealing the lowest layers of a underground mine roof to upper strata of rock. The most common and effective means for attaching lower level rock strata to upper layers is to utilize a roof bolt and epoxy resin to seal the various layers of rock strata. Roof bolts vary in length and diameter but are typically one-half inch or more in diameter and 30 inches to 12 feet long or longer in overall length. To place a roof bolt in a roof ceiling, a motorized roof bolter, such as that manufactured commercially by such companies as Fletcher Mining Equipment Company, is positioned in the front, unprotected face of the mine and features a drilling mechanism to drill several feet up through the mine roof. After a hole is placed in the roof, an epoxy resin in a pliable plastic tube is inserted in the hole. Next, a roof bolt is placed in the hole, and the placing of the roof bolt tears the packaging for the epoxy resin and mixes said resin to the bolt itself and the surrounding rock layers. The epoxy resin typically "sets up" or hardens within a matter of seconds and the bolt and rock layers are thereby sealed to each other.

In most underground mining situations, a roof bolt is placed approximately every four feet in the mine. Accordingly, placement of roof support is a major undertaking and a major source of expense for the mine operator. Despite the cost, roof bolt/epoxy combinations are the most effective and practical means for providing primary roof support, and fully meet the requirements promulgated by MSHA and various state enforcement authorities.

A key limitation to the effectiveness of resin-based systems is the presence of drawrock. Drawrock refers to thin layers of shale, one inch to twenty inches thick, which is frequently found throughout the United States immediately adjacent and above seams of coal. In such scenarios, as coal is underground mined, the immediate roof material may consist of several inches or feet of shale or drawrock. Shale may be very hard in the compressed state, and a underground mine roof characterized by shale usually is a very stable roof when the mine is first opened and the adjoining seam of coal first removed. However, when shale is exposed to the elements, i.e. moisture, the characteristics of the rock begin to change. Over a period of time, wet shale may begin to deteriorate into drawrock, and the layers of rock will separate. As this occurs, the lower, exposed layers will crumble and begin flaking off and dropping. It is quite typical that the inside of a mine will be wet, and often a substantial amount of water will be encountered. Accordingly, drawrock can be a major problem in a wet underground mine which is characterized by a shale roof or upper walls. While primary roof control is normally quite effective in securing various strata of rock together for three to six foot lengths, crumbling drawrock in the lower layer ca mine the protection.

A roof bolt properly anchored in an epoxy-based resin effectively supports the roof because it applies upward pressure to hold the various strata of rock together in an essentially compressed state. At the exposed end of the bolt, a base plate, typically 8 inches by 8 inches, is anchored against the roof by the bolt. This base plate supports the lowest roof layer while the bolt anchors the lower strata to upper strata of rock.

The presence of drawrock can seriously underground mine a primary roof support system. If the immediate roof layer (just above the base plate) is drawrock, deterioration of the drawrock by environmental conditions can result in a crumbling of the roof in the vicinity of the base plate. Accordingly, the rock layer just about the base plate may crumble and flake away over time. When this occurs, the roof support system is compromised because in order for the system to be effective, the base plate must be applying pressure against the lower strata of rock anchoring them to upper rock layers. If drawrock crumbles in the vicinity of the base plate, the roof support system at that point consists only of a bolt in epoxy gluing the upper strata together. No pressure is being applied by the base plate. This may result in the lower rock strata becoming loose and falling.

State and Federal underground mine inspection officials are aware that the presence of drawrock can mine a roof bolt support system in a mine. When the presence of drawrock results in a flaking away of the rock strata just above the base plate, inspection officials will require the mine operator to install another roof bolt or provide some other means for achieving primary roof support in that vicinity. For the mine operator, this is a very expensive problem, because it means the operator will have to bring a roof bolter into this area of the mine to install a new bolt. Since the drawrock deterioration may occur months or years after the installation of the initial roof bolt, roof bolters are typically nowhere near the area of the mine in which drawrock has created the need to re-install a bolt. The manpower requirements to move a roof bolt installation machine from remote areas of the mine back to areas previously underground mined may result in considerable downtime. However, the work has to be done because the drawrock damaged area of the mine is essentially devoid of primary roof support and the dangers associated with this condition are unacceptable.

The danger may be even more pronounced considering that the older portions of the mine, where roof bolts were installed years earlier, are now typically passageways for access to new work areas of the mine. As such, it may be a major traffic thoroughfare for underground miners and equipment. A crumbling of the ceiling in this area, therefore, can result in a localized roof fall in a part of the mine more likely to affect personnel and equipment.

Some portions of an open underground mine may not be accessed by a roof bolter without closing the entire underground mine. For example, if a conveyor belt has been placed in a portion of a underground mine passageway, one cannot relocate a roof bolter into that passageway to replace roof bolts unless the conveyor belt is removed. In some areas, wooden cribbing material or other structures might also have to be moved at considerable cost. In addition, some areas of the mine, due to moisture or traffic, may have experienced a softening of the mine floor such that the floor cannot support the added weight of roof bolting machinery in the area. In such a circumstance, the mine operator would be forced to excavate the soft floor material and replace it with rock or concrete in order to build up a floor that will support the roof bolting equipment. Of course, during the period of time that the floor is being repaired or poured, the workers are exposed to the weakened roof condition that precipitated the need for repairs in the first place.

Furthermore, abandoned underground mine sites can be great safety hazards. Each year, a number of people are killed or injured nationally in abandoned underground mines. Many of these structures contain dilapidated frames, open shafts, and water-filled pits. The dangers that may be found in the mines include old explosives, hazardous chemicals, snakes, spiders, mice, and bats. For example, an entrance may place a person at risk for hazards such as falls and cave-ins. Visitors also find these areas as accessible dumping grounds for trash. This can cause infestations and contact with wild animals. In the process of dumping into these underground mines, many slips and falls are incurred, which can lead to entrapment in the mines, serious injuries and possible death. The mineral deposits can cause contamination to the surrounding water systems. Some of these systems may serve as municipal water supplies for nearby citizens. The Forest Service, along with other land management agencies, is involved in ensuring the safety of the water supply and preventing contact with contaminated waters.

Figure 2:
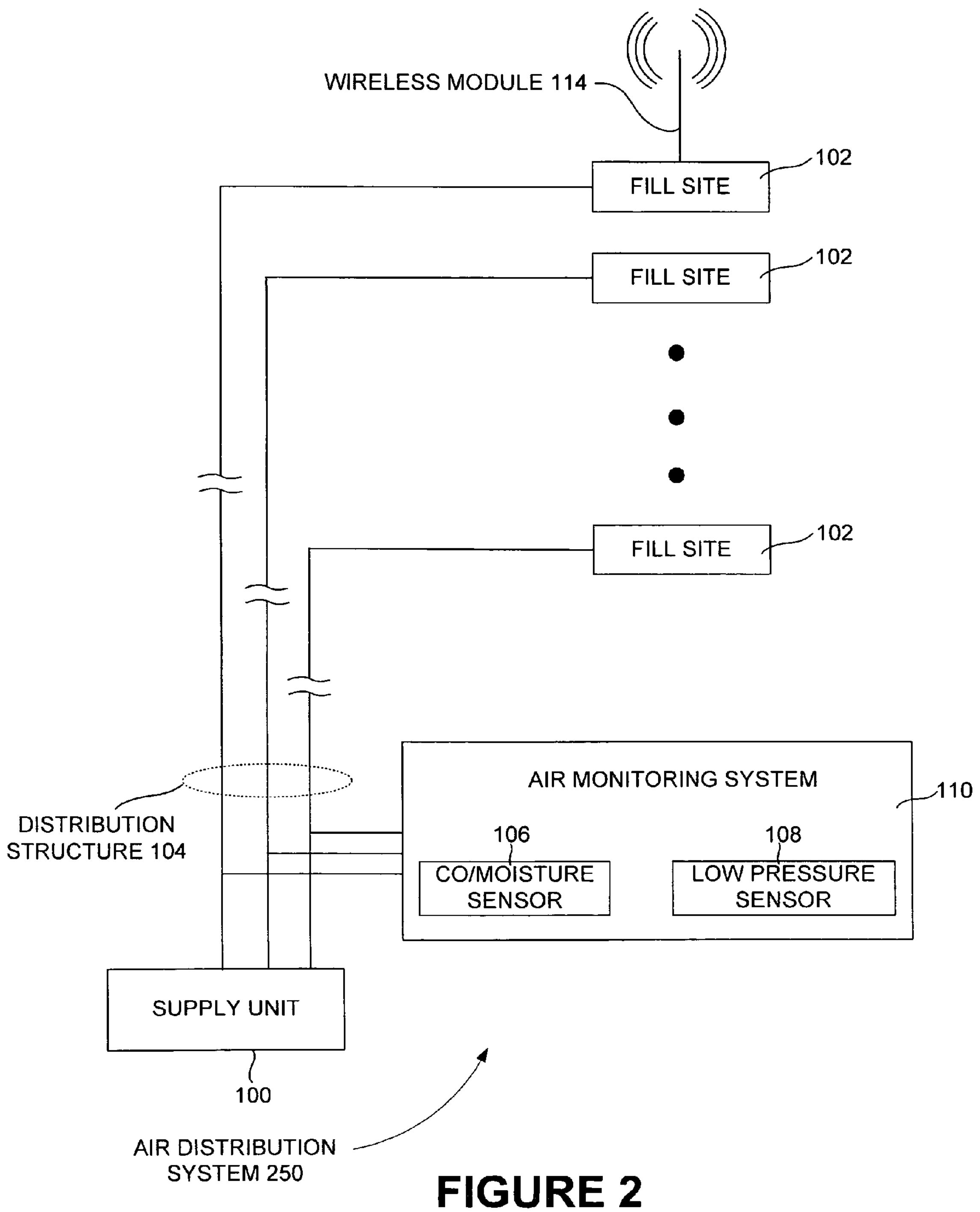
FIG. 2 is another diagram of an air distribution structure in a underground mine structure, according to one embodiment.
Figure 3:
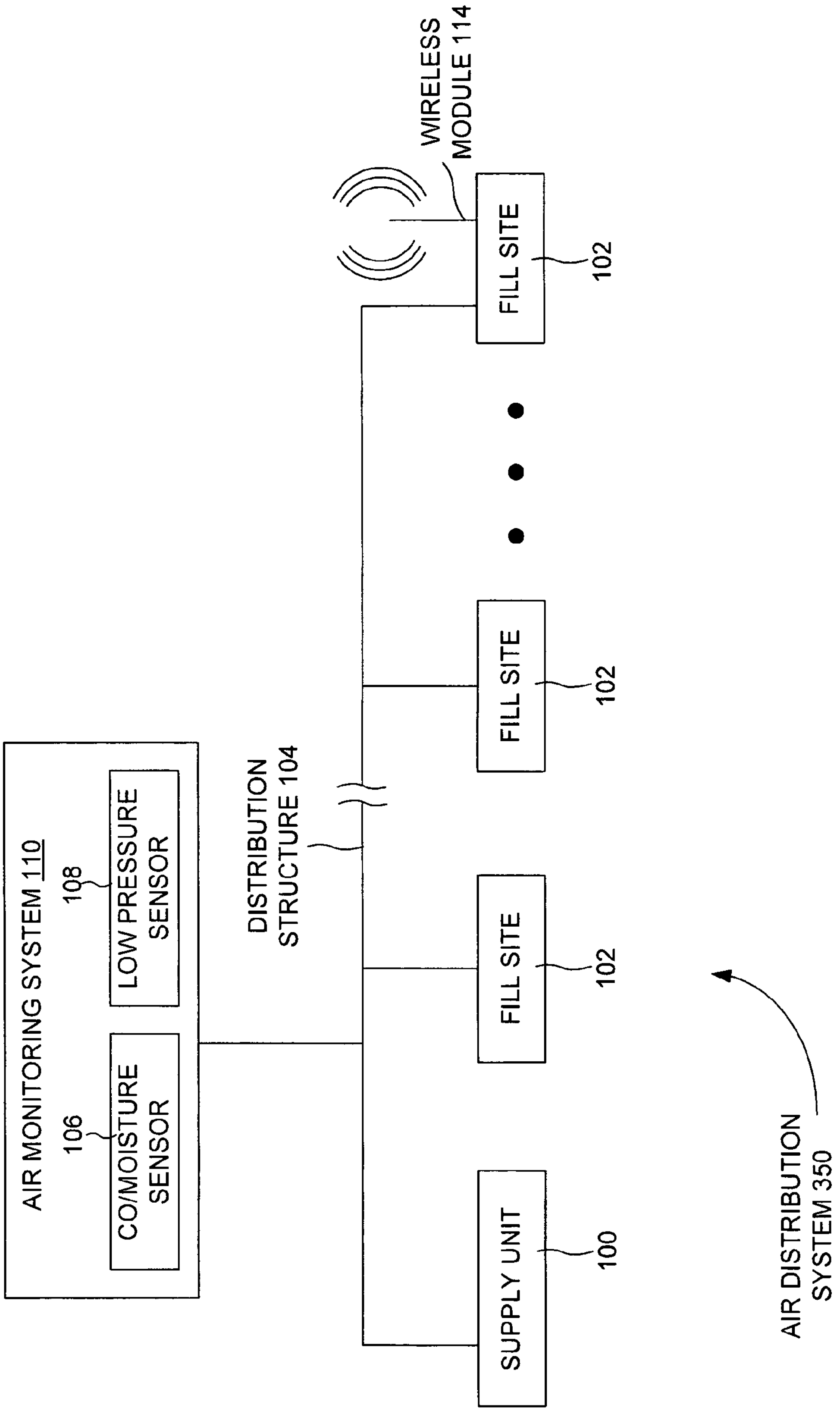
FIG. 3 is a diagram of an air distribution structure in a underground mine structure having fill sites located horizontally from one another, according to one embodiment.

In one embodiment, a safety system of a underground mine structure includes an supply unit (e.g., an supply unit 100 of FIGS. 1-3) of a underground mine structure to facilitate delivery of breathable air from a source of compressed air to an air distribution structure (e.g., an air distribution system 150, 250, 350 of FIGS. 1-3) of the mine structure wherein the supply unit (e.g., an supply unit 100 of FIGS. 1-3) includes a check valve (e.g., a check valve of a series of valves 410 of FIG. 4) to prevent a leakage of the breathable air from the air distribution structure (e.g., the air distribution system 150, 250, 350 of FIGS. 1-3) potentially leading to loss of a system pressure, a fill site (e.g., a fill site 102B of FIG. 6B, and/or a fill station 102A of FIG. 6A) interior to the mine structure to provide the breathable air to a breathable air apparatus at multiple locations of the mine structure, a secure chamber housing the fill site (e.g., the fill site 102B of FIG. 6B, and/or the fill station 102A of FIG. 6A) as a protective placement of the fill site (e.g., the fill site 102B of FIG. 6B, and/or the fill station 102A of FIG. 6A) to provide a safety shield from an over-pressurized breathable air apparatus, a distribution structure (e.g., a distribution structure 104 of FIGS. 1-3) that is compatible with use with compressed air to couple the supply unit (e.g. the supply unit 100 of FIGS. 1-3) and the fill site (e.g., the fill site 102B of FIG. 6B, and/or the fill station 102A of FIG. 6A) to transfer the breathable air from the source of compressed air to the fill station, and/or an air storage sub-system (e.g., an air storage sub-system 1050 of FIG. 9) to provide an additional supply of breathable air in addition to the source of compressed air of FIGS. 1-3) include stainless steel that is compatible for use with compressed air.

In another embodiment, a method may include ensuring that a prescribed pressure of the emergency support system (e.g., the air distribution system 150, 250, 350 of FIGS. 1-3) maintains within a threshold range of the prescribed pressure by including a valve of an supply unit (e.g., the supply unit 100 of FIGS. 1-3) to prevent leakage of breathable air from the emergency support system (e.g., the air distribution system 150, 250, 350 of FIGS. 1-3), safeguarding a filling process of a breathable air apparatus by enclosing the breathable air apparatus in a secure chamber of a fill site (e.g., a fill site 102B of FIG. 6B, and/or a fill station 102A of FIG. 6A) of the emergency support system (e.g., the air distribution system 150, 250, 350 of FIGS. 1-3) of the mine structure to provide a safe placement to supply the breathable air to the breathable air apparatus, and/or providing a spare storage of breathable air through a plurality of air storage tanks (e.g., the air storage tanks 1008 of FIG. 10) of a storage sub-system (e.g., the air storage sub-system 1050 of FIG. 10) to store breathable air that is able to be replenished by a source of compressed air.

FIG. 1 is a diagram of an air distribution system 150 in a mine structure, according to one embodiment. The air distribution system 150 may include any number of supply unit 100, any number of fill site 102 (e.g., a fill panel and/or a fill station, etc.) that are coupled to the rest of the air distribution system 150 through a distribution structure 104. The air distribution system 150 may also include a air monitoring system 110 having a CO/Moisture sensor 106 and a pressure sensor 108. The supply unit 100 may be placed at a number of locations exterior to the mine structure (e.g., a horizontal mine structure such as a shopping mall, IKEA, Home Depot, a vertical mine structure such as a high rise building, a mid rise building, and/or a low rise building, a mine, a subway, and/or a tunnel, etc.) to allow ease of access by a source of compressed air and/or to expedite supplying the air distribution system 150 with breathable air. The supply unit 100 may also be placed at locations that are substantially free of traffic (e.g., parked cars, vehicle movement, and/or human traffic, etc.) to decrease potential obstruction that may be present in an emergency situation (e.g., a building fire, a chemical attack, terror attack, subway accident, mine collapse, and/or a biological agent attack, etc.).

The fill site 102 may also be placed at a number of locations of the mine structure (e.g., a horizontal mine structure such as a shopping mall, IKEA, Home Depot, a vertical mine structure such as a high rise building, a mid rise building, and/or a low rise building, a mine, a subway, and/or a tunnel, etc.) to provide multiple access points to breathable air in the mine structure. The mine structure may have any number of fill site 102 (e.g., a fill panel and/or a fill station, etc.) on each floor and/or have fill site 102 (e.g., a fill panel and/or a fill station, etc.) on different floors. Each fill site 102 may be sequentially coupled to one another and to the supply unit 100 through the distribution structure 104. The distribution structure 104 may include any number of pipes to expand an air carrying capacity of the air distribution system 150 such that breathable air may be replenished at a higher rate. In addition, the fill site 102 may include wireless capabilities (e.g., a wireless module 114) for communication with remote entities (e.g., the supply unit 100, building administration, and/or an authority agency, etc.).

The air monitoring system 110 may contain multiple sensors such as the CO/moisture sensor 106 and the pressure sensor 108 to track air quality of the breathable air in the air distribution system 150. Since emergency personnel (e.g., a fire fighter, a SWAT team, a law enforcer, and/or a medical worker, etc.) depend on the breathable air distributed via the air distribution system 150, it is crucial that air quality of the breathable air be constantly maintained. The air monitoring system 110 may also include other sensors that detect other hazardous substances (e.g., benzene, acetamide, acrylic acid, asbestos, mercury, phosphorous, propylene oxide, etc.) that may contaminate the breathable air.

In one embodiment, the distribution structure 104 may be compatible with use with compressed air facilitates dissemination of the breathable air of the source of compressed air to multiple locations of the mine structure. A fire rated material may encase the distribution structure 104 such that the distribution structure has the ability to withstand elevated temperatures for a period of time. The pipes of the distribution structure 104 may include a sleeve exterior to the fire rated material to further protect the fire rated material from any damage. Both ends of the sleeve may be fitted with a fire rated material that is approved by an authority agency. In addition, the distribution structure 104 may include a robust solid casing to prevent physical damage to the distribution structure potentially compromising the safety and integrity of the air distribution system.

The distribution structure 104 may include support structures at intervals no larger than five feet to provide adequate structural support for each pipe of the distribution structure 104. The pipes and the fittings of the distribution structure 104 may include any of a stainless steel and a thermoplastic material that is compatible for use with compressed air.

In another embodiment, the air distribution system may include an air monitoring system (e.g., the air monitoring system 110) to automatically track and record any impurities and contaminants in the breathable air of the air distribution system. The air monitoring system (e.g., the air monitoring system 110) may have an automatic shut down feature to suspend air distribution to the fill site 102 in a case that any of an impurity and contaminant concentration exceeds a safety threshold. For example, a pressure monitoring system (e.g., the pressure sensor 108) may automatically track and record the system pressure of the air distribution system. Further, a pressure switch may be electrically coupled to a alarm system such that the fire alarm system is set off when the system pressure of the air distribution system is outside a safety range.

FIG. 2 is another diagram of an air distribution system 250 in a mine structure, according to one embodiment. The air distribution system 250 may include any number of supply unit 100, any number of fill site 102 (e.g., a fill panel and/or a fill station, etc.) that are coupled to the rest of the air distribution system 150 through a distribution structure 104. The air distribution system 150 may also include a air monitoring system 110 having a CO/Moisture sensor 106 and a pressure sensor 108. In the air distribution system 250, the distribution structure 104 may individually couple each fill site 102 (e.g., a fill panel and/or a fill station, etc.) to a supply unit 100. Individual coupling may be advantageous in that in the case one pipe of the distribution structure 104 becomes inoperable the other pipes can still deliver air to the fill site 102 (e.g., a fill panel and/or a fill station, etc.). The other system components (e.g., the fill site 102, the supply unit 100, and the air monitoring system 110 were described in detail in the previous section).

FIG. 3 is a diagram of an air distribution system 350 in a mine structure having fill site 102 (e.g., a fill panel and/or a fill station, etc.) located horizontally from one another, according to one embodiment.

The air distribution system 350 may include any number of supply unit 100, any number of fill site 102 (e.g., a fill panel and/or a fill station, etc.) that are coupled to the rest of the air distribution system 150 through a distribution structure 104. The air distribution system 150 may also include a air monitoring system 110 having a CO/Moisture sensor 106 and a pressure sensor 108. In the air distribution system 250, the distribution structure 104 may sequentially couple each fill site 102 (e.g., a fill panel and/or a fill station, etc.) displaced predominantly horizontally from a supply unit 100. Each air distribution system (e.g., the air distribution system 150, 250, 350) may be used in conjunction with one another depending on the particular architectural style of the mine structure in a manner that provides most efficient access to the breathable air of the air distribution system reliably. The other system components (e.g., the fill site 102, the supply unit 100, and the air monitoring system 110 were described in detail in the previous section).

FIG. 4A is a front view of a supply unit 100, according to one embodiment.

The supply unit 100 provides accessibility of a source of compressed air to supply air to an air distribution system (e.g., an air distribution system 150, 250, and/or 350). The supply unit may include a fill pressure indicator 400, a fill control knob 402, a system pressure indicator 404, a connector 406, and/or a supply unit enclosure 408. The fill pressure indicator 400 may indicate the pressure level at which breathable air is being delivered by the source of compressed air to the air distribution system (e.g., an air distribution system 150, 250, and/or 350 of FIGS. 1-3). The system pressure indicator 404 may indicate the current pressure level of the breathable air in the air distribution system. The fill control knob 402 may be used to control the fill pressure such that the fill pressure does not exceed a safety threshold that the air distribution system is designed for. The connector 406 may be a CGA connector that is compatible with an air outlet of the source of compressed air of various emergency agencies (e.g., fire station, law enforcement agency, medical provider, and/or SWAT team, etc.). The connector 406 of the supply unit 100 may facilitate a connection with the source of compressed air through ensuring compatibility of the supply unit 100 with the source of compressed air.

The supply unit 100 may include an adjustable pressure regulator of the supply unit 100 that is used to adjust a fill pressure of the source of compressed air to ensure that the fill pressure does not exceed the design pressure of the air distribution system. Further, the supply unit may also include at least one pressure gauge of the supply unit enclosure 408 to indicate any of the system pressure (e.g., the system pressure indicator 404) of the air distribution system and the fill pressure (e.g., the fill pressure indicator 400) of the source of compressed air.

FIG. 4B is a rear view of a supply unit 100, according to one embodiment.

The supply unit also includes a series of valves 410 (e.g., a valve, an isolation valve, and/or a safety relief valve, etc.) to further ensure that system pressure is maintained within a safety threshold of the design pressure of the air distribution system.

The supply unit 100 of a mine structure may facilitate delivery of breathable air from a source of compressed air to an air distribution system of the mine structure. The supply unit 100 includes the series of valves 410 (e.g., the valve, the safety relief valve, etc.) to prevent a leakage of the breathable air from the air distribution system potentially leading to loss of a system pressure. For example, the supply unit 100 may include the valve of the series of valves 410 to automatically suspend transfer of breathable air from the source of compressed air to the air distribution system when useful. The safety relief valve of the supply unit 100 and/or the fill site 102 may release breathable air when a system pressure of the air distribution system exceeds a threshold value beyond the design pressure to ensure reliability of the air distribution system through maintaining the system pressure such that it is within a pressure rating of each component of the air distribution system.

Figure 5:
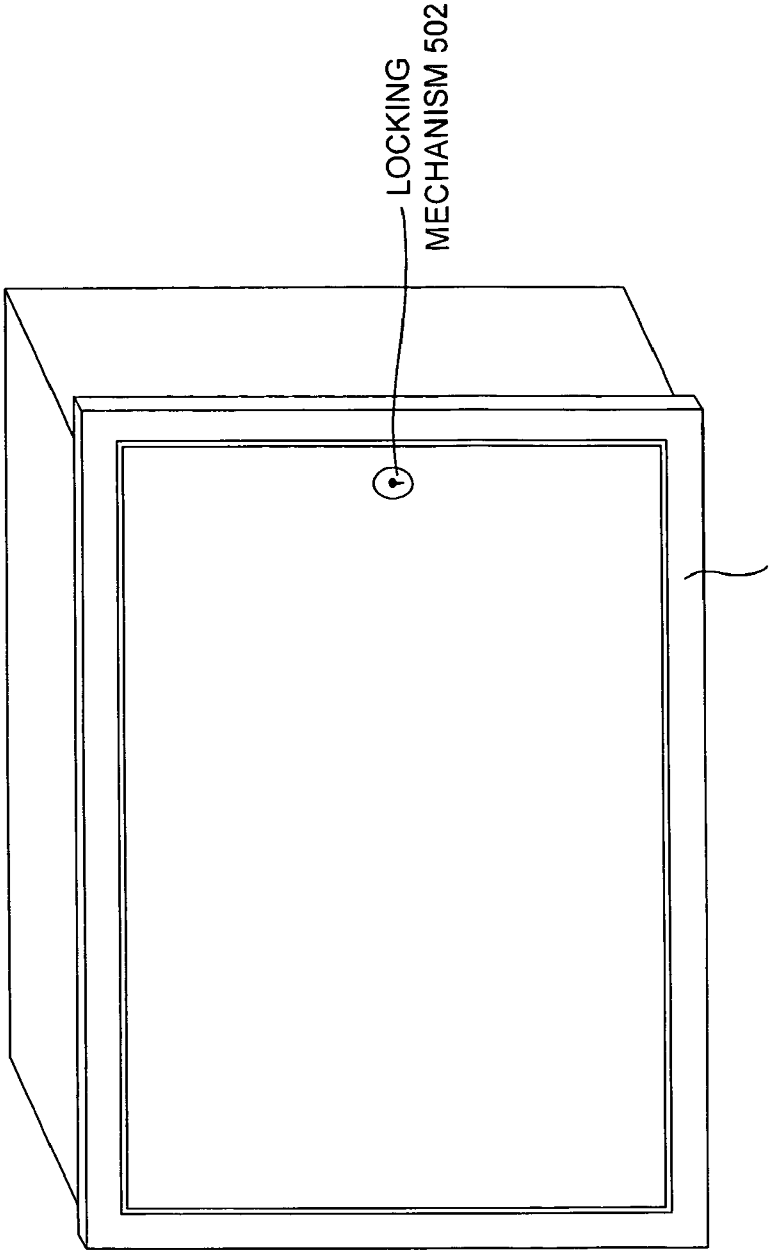
FIG. 5 is an illustration of a supply unit enclosure, according to one embodiment.

FIG. 5 is an illustration of a supply unit enclosure 500, according to one embodiment.

The supply unit enclosure 500 may include a locking mechanism 502 to secure the supply unit 100 from unauthorized access. Further, the supply unit enclosure 500 may also contain fire rated material such that the supply unit 100 is able to withstand burning elevated temperatures.

The supply unit enclosure 500 encompassing the supply unit 100 may have any of a weather resistant feature, ultraviolet and infrared solar radiation resistant feature to prevent corrosion and physical damage. The locking mechanism 502 may secure the supply unit from intrusions that potentially compromise safety and reliability of the air distribution system. In addition, the supply unit enclosure 500 may include a robust metallic material of the supply unit enclosure 500 to minimize a physical damage due to various hazards to protect the supply unit 100 from any of an intrusion and damage. The robust metallic material may be at least substantially 18 gauge carbon steel. The supply unit enclosure 500 may include a visible marking to provide luminescence in a reduced light environment. The locking mechanism 502 may also include a tamper switch such that a alarm is automatically triggered and a signal is electrically coupled to any of a relevant administrative personnel of the mine structure and the emergency supervising station when an intrusion of any of the supply unit and the secure chamber occurs.

Figure 6A:
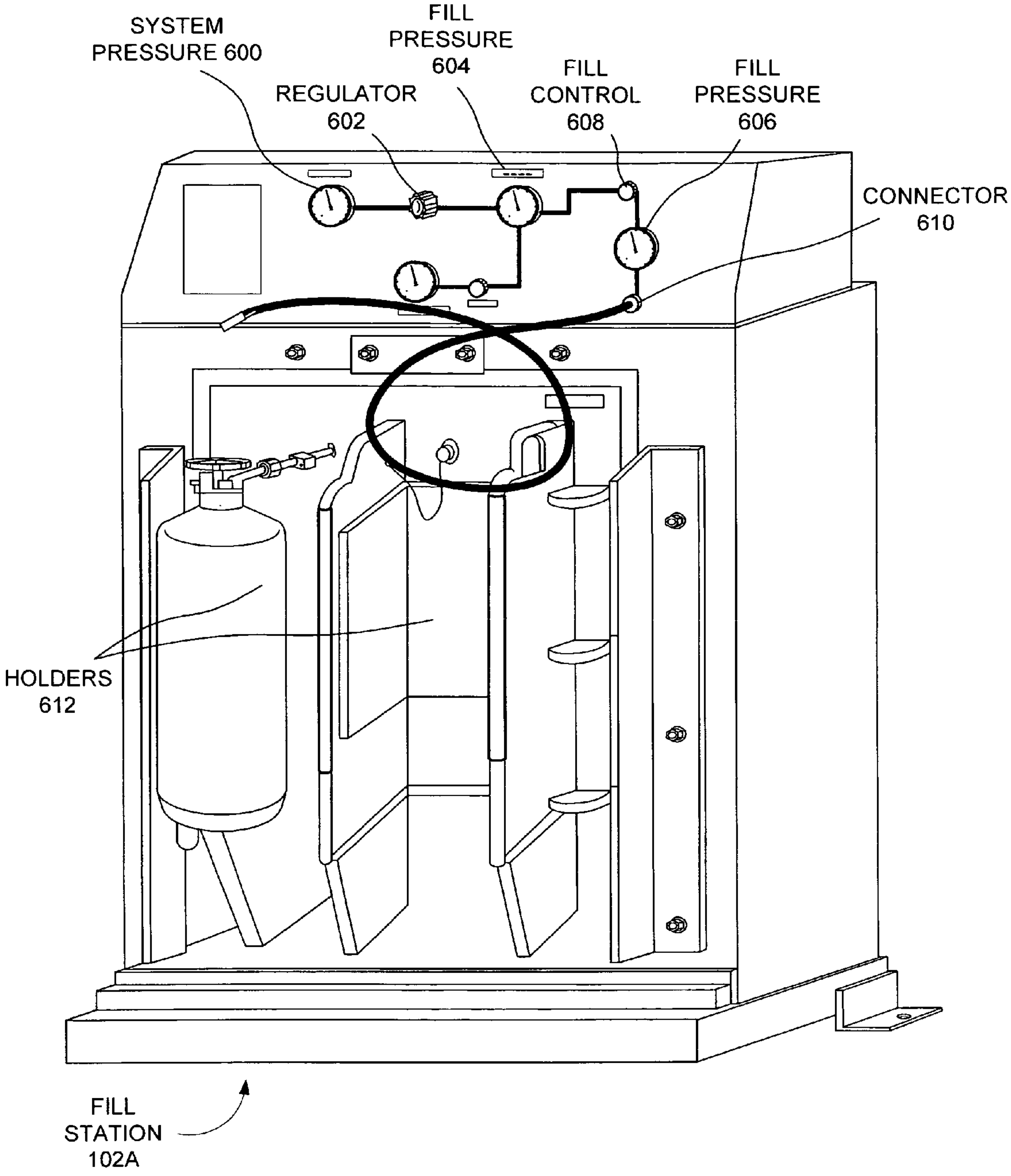
FIG. 6A is an illustration of a fill station, according to one embodiment.

FIG. 6A is an illustration of a fill station 102A, according to one embodiment.

The fill station 102A may be a type of fill site 102 of FIG. 1. The fill station 102A may include a system pressure indicator 600, a regulator 602, a fill pressure indicator 604, another fill pressure indicator 606, a fill control knob 608, a connector 610 (e.g., a RIC/UAC connector), and a multiple breathable air apparatus holders 612. The connector 610 and the multiple breathable air apparatus holders 612 may be used to supply air from the air distribution system. The fill pressure indicator 604 may indicate the pressure level at which breathable air is being delivered by the source of compressed air to the air distribution system (e.g., an air distribution system 150, 250, and/or 350 of FIGS. 1-3). The system pressure indicator 600 may indicate the current pressure level of the breathable air in the air distribution system. The fill control knob 608 may be used to control the fill pressure such that the fill pressure does not exceed a safety threshold that the air distribution system is designed for. The connector 610 may facilitate direct coupling to emergency equipment to supply breathable air through a hose that is connected to the connector 610. In essence, precious time may be saved because the emergency personnel may not need to spend the time to remove the emergency equipment from their rescue attire before they can be supplied with breathable air. Further, the connector 610 may also directly couple to a face-piece of a respirator to supply breathable air.

The multiple breathable air apparatus holders 612 can hold multiple compressed air cylinders to be filled simultaneously. In addition, the multiple breathable air apparatus holders 612 can be rotated such that additional compressed air cylinders may be loaded while the multiple compressed air cylinders are filled inside the fill station 102A. The fill station 102A may be a rupture containment chamber such that over-pressurized compressed air cylinders are shielded and contained to prevent injuries.

In one embodiment, the fill station 102A interior to the mine structure may provide the breathable air to a breathable air apparatus at multiple locations of the mine structure. A secure chamber of the fill station 102A may be a safety shield that confines a possible rupture of an over-pressurized breathable air apparatus within the secure chamber. The fill station 102A may include a valve to prevent leakage of air from the air distribution system potentially leading to pressure loss of the air distribution system through ensuring that the system pressure is maintained within a threshold range of the design pressure to reliably fill the breathable air apparatus. An isolation valve may be included to isolate a breathable fill station from a remaining portion of the air distribution system.

The isolation valve may be automatically actuated based on an air pressure sensor of the air distribution system. The fill station 102A may include at least one pressure regulator to adjust a fill pressure to fill the breathable air apparatus and to ensure that the fill pressure does not exceed the pressure rating of the breathable air apparatus potentially resulting in a rupture of the breathable air apparatus. The fill station 102A may include at least one pressure gauge to indicate any of a fill pressure (e.g., the fill pressure indicator 604, 606) of the fill station and a system pressure (e.g., the system pressure indicator 600) of the air distribution system. In one embodiment, the fill station 102A may have a physical capacity to enclose at least one breathable air apparatus and may include a RIC (rapid interventions company/crew)/UAC (universal air connection connector to facilitate a filling of the breathable air apparatus. The fill station may also include a securing mechanism of the secure chamber of the fill station having a locking function is automatically actuated via a coupling mechanism with a flow switch that indicates a status of air flow to the breathable air apparatus that is tillable in the fill station.

Figure 6B:
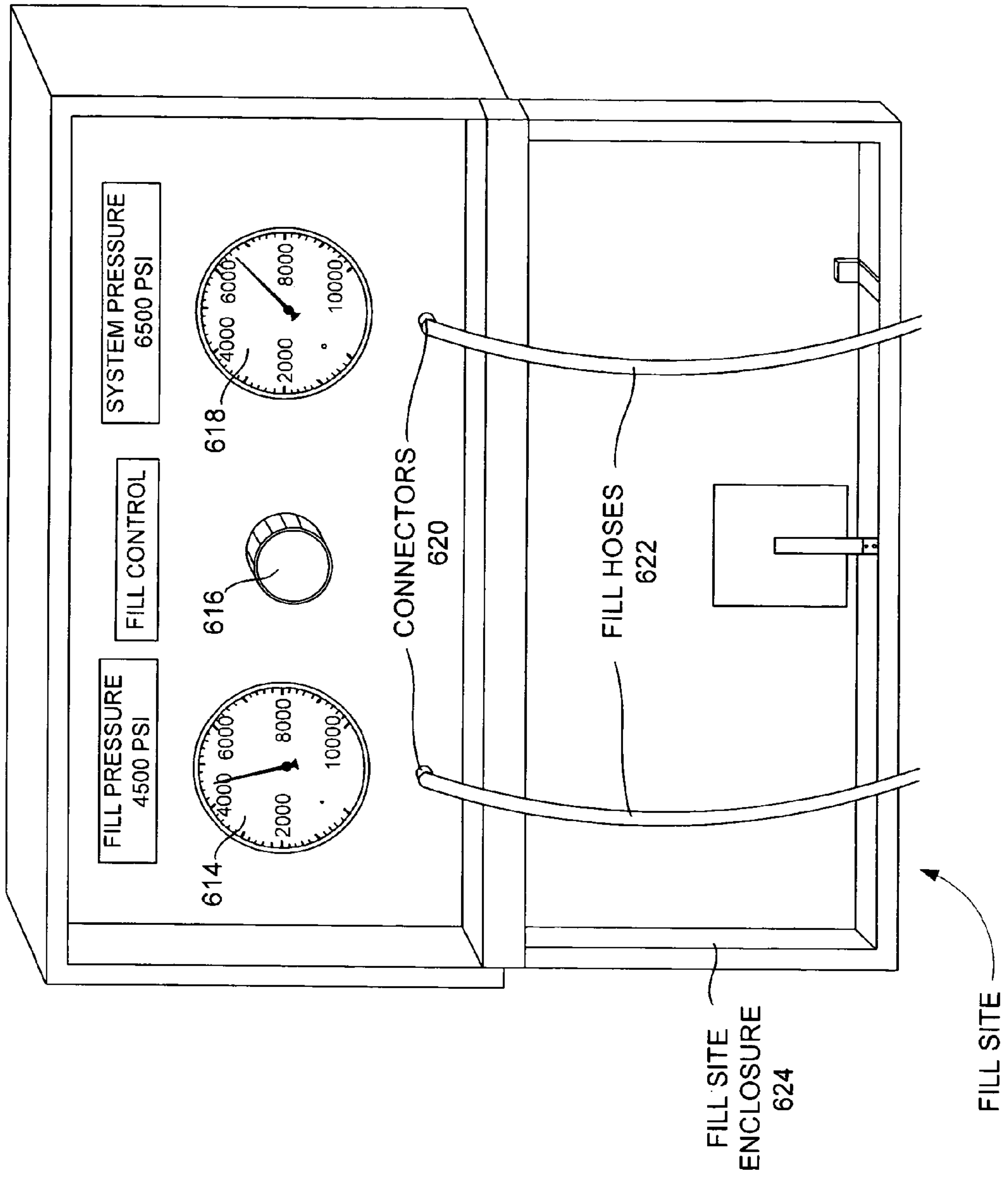
FIG. 6B is an illustration of a fill site, according to one embodiment.

FIG. 6B is an illustration of a fill site 102B, according to one embodiment.

The fill site 102B (e.g., a fill panel) includes a fill pressure indicator 614 (e.g., pressure gauge), a fill control knob 616 (e.g., pressure regulator), a system pressure indicator 618, a number of connectors 620 (e.g., a number of RIC (rapid interventions company/crew)/UAC (universal air connection) connectors), and/or fill hoses 622. The fill site 102B may also include a locking mechanism of a fill site enclosure 624 (e.g., a fill panel enclosure) to secure the fill panel from intrusions that potentially compromise safety and reliability of the air distribution system. The system pressure indicator 618 may indicate the current pressure level of the breathable air in the air distribution system. The fill control knob 616 (e.g., pressure regulator) may be used to adjust the fill pressure such that the fill pressure does not exceed a safety threshold that the air distribution system is designed for.

The connectors 620 may facilitate direct coupling to emergency equipment to supply breathable air through the fill hoses 622 that are connected to the connectors 620. In essence, precious time may be saved because the emergency personnel may not need to spend the time to remove the emergency equipment from their rescue attire before they can be supplied with breathable air. Further, the connectors 620 connected with the fill hoses 622 may also directly couple to a face-piece of a respirator to supply breathable air to either emergency personnel (e.g., a fire fighter, a SWAT team, a law enforcer, and/or a medical worker, etc.) and/or stranded survivors in need of breathing assistance. Each of the fill hoses 622 may have different pressure rating of the fill site 102B is coupleable to any of a self-contained breathable air apparatus and respiratory mask having a compatible RIC/UAC connector. The fill panel enclosure may include a visible marking to provide luminescence in a reduced light environment.

The fill site 102B interior to the mine structure may have the connectors 620 (e.g., RIC (rapid interventions company/crew)/UAC (universal air connection) connectors) to fill a breathable air apparatus to expedite a breathable air extraction process from the air distribution system and to provide the breathable air to the breathable air apparatus at multiple locations of the mine structure. The fill site 102B may include a safety relief valve set to have an open pressure of at most approximately 10% more than a design pressure of the air distribution system to ensure reliability of the air distribution system through maintaining the system pressure such that it is within a threshold range of a pressure rating of each component of the air distribution system.

The fill site enclosure 624 may comprise of at least 18 gauge carbon steel to minimize physical damage of various naturally occurring and man-imposed hazards through protecting the fill panel from any of an intrusion and damage. The fill site 102B may include an isolation valve to isolate a damaged fill panel from a remaining operable portion of the air distribution system.

Figure 7A:
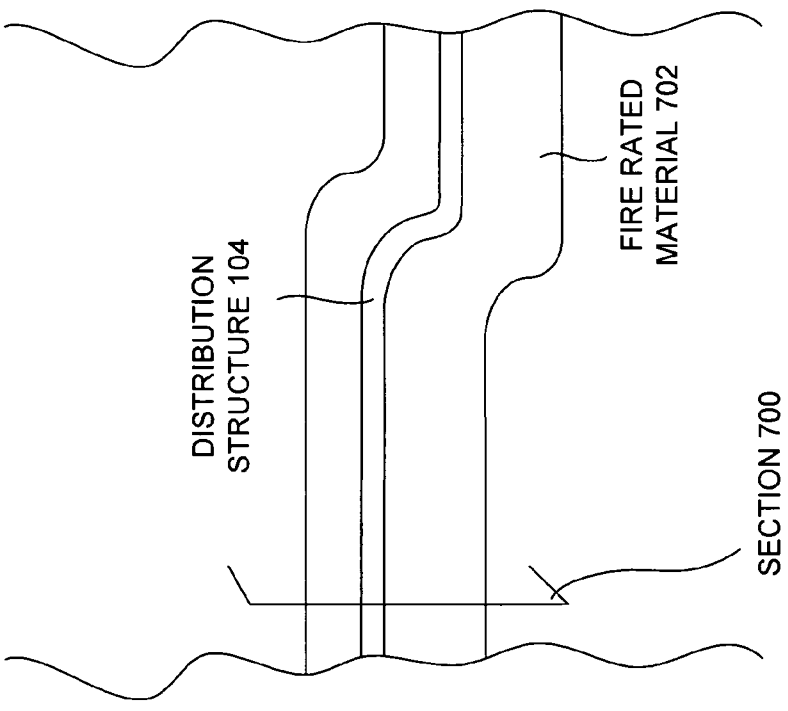
FIG. 7A is a diagrammatic view of a distribution structure embedded in a fire rated material, according to one embodiment.

FIG. 7A is a diagrammatic view of a distribution structure 104 embedded in a fire rated material 702, according to one embodiment.

The distribution structure 104 may be enclosed in the fire rated material 702. The fire rated material may prevent the distribution structure 104 from damage in a fire such that an air distribution system (e.g., the air distribution system 150, 250, 350 of FIGS. 1-3) may be operational for a longer time period in an emergency situation (e.g., a building fire, a chemical attack, terror attack, subway accident, mine collapse, and/or a biological agent attack, etc.). Section 700 is a cross section of the distribution structure 104 embedded in the fire rated material 702.

Figure 7B:
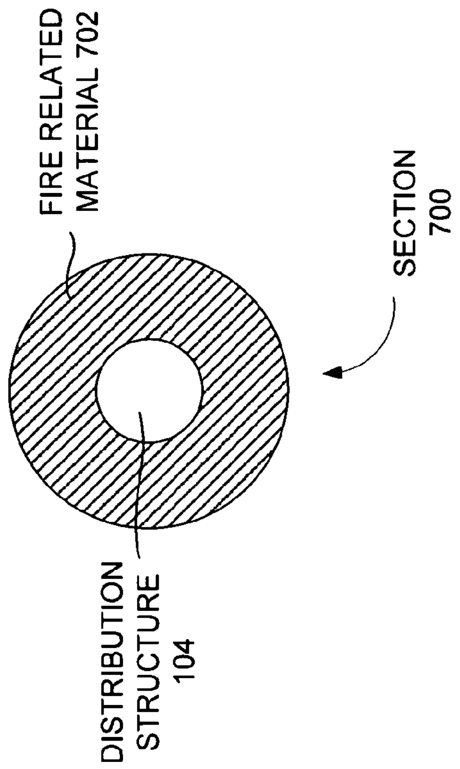
FIG. 7B is a cross sectional view of a distribution structure embedded in a fire rated material, according to one embodiment.

FIG. 7B is a cross sectional view 700 of a distribution structure 104 embedded in a fire rated material 702, according to one embodiment.

Section 700 is a cross section of the distribution structure 104 embedded in the fire rated material 702.

Figure 8:
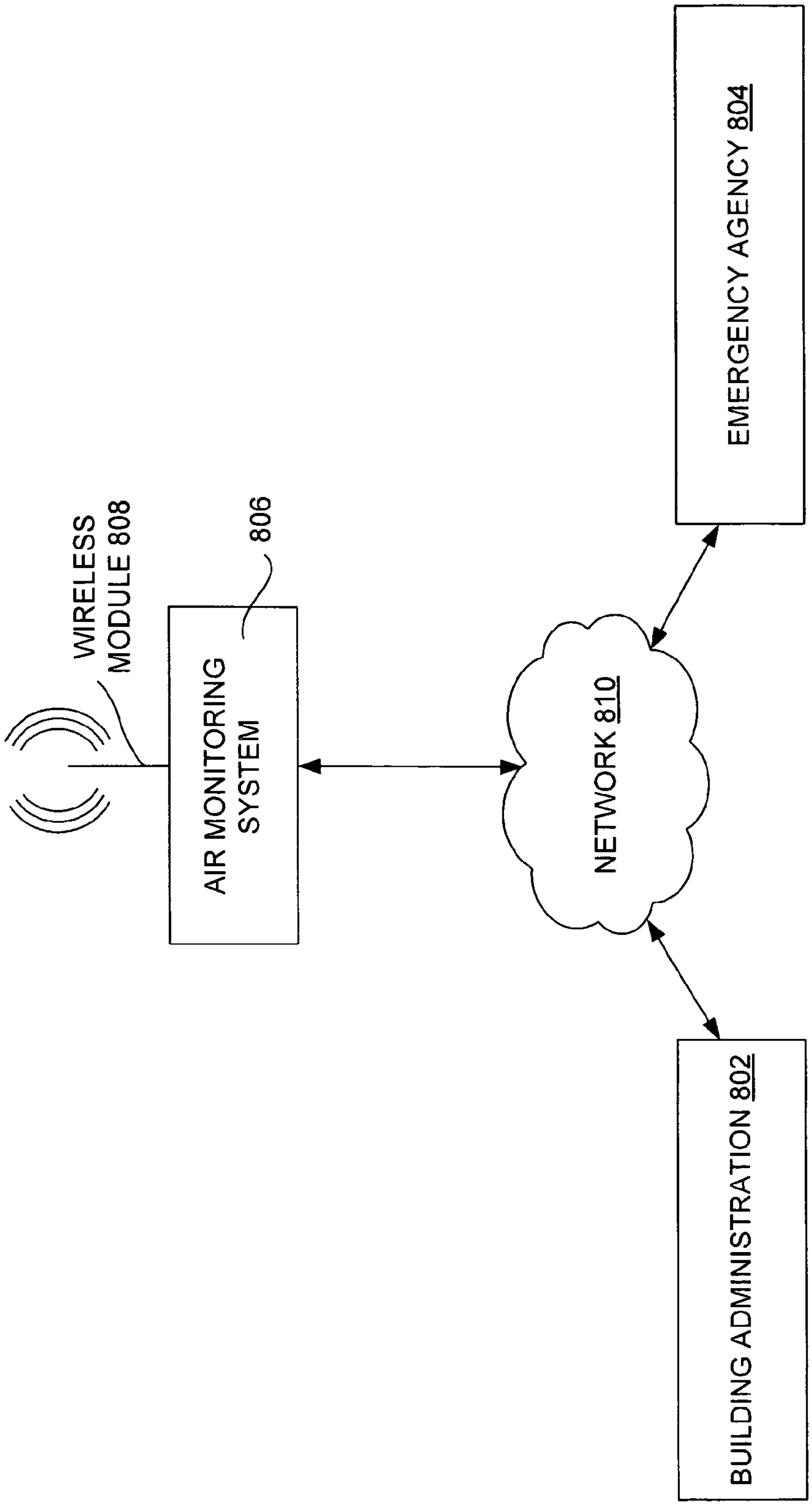
FIG. 8 is a network view of a air monitoring system that communicates building administration and an emergency agency, according to one embodiment.

FIG. 8 is a network view of a air monitoring system 806 with a wireless module 808 that communicates with a building administration 802 and an authority agency 804 through a network 810, according to one embodiment.

The air monitoring system 806 may include various sensors (e.g., CO/moisture sensor 106 of FIG. 1, pressure sensor 108 of FIG. 1, and/or hazardous substance sensor, etc.) and/or status indicators regarding system readiness information (e.g., system pressure, in use, not in use, operational status, fill site usage status, fill site operational status, etc.). The air monitoring system 806 may communicate sensor readings to a building administration 802 (e.g., building management, security, and/or custodial services, etc.) such that proper maintenance measures may be taken. The air monitoring system 806 may also send alerting signals as a reminder for regular system inspection and maintenance to the building administration 802 through the network 810. The air monitoring system 806 may also communicate sensor readings to an authority agency 804 (e.g., a police station, a fire station, and/or a hospital, etc.).

Figure 9:
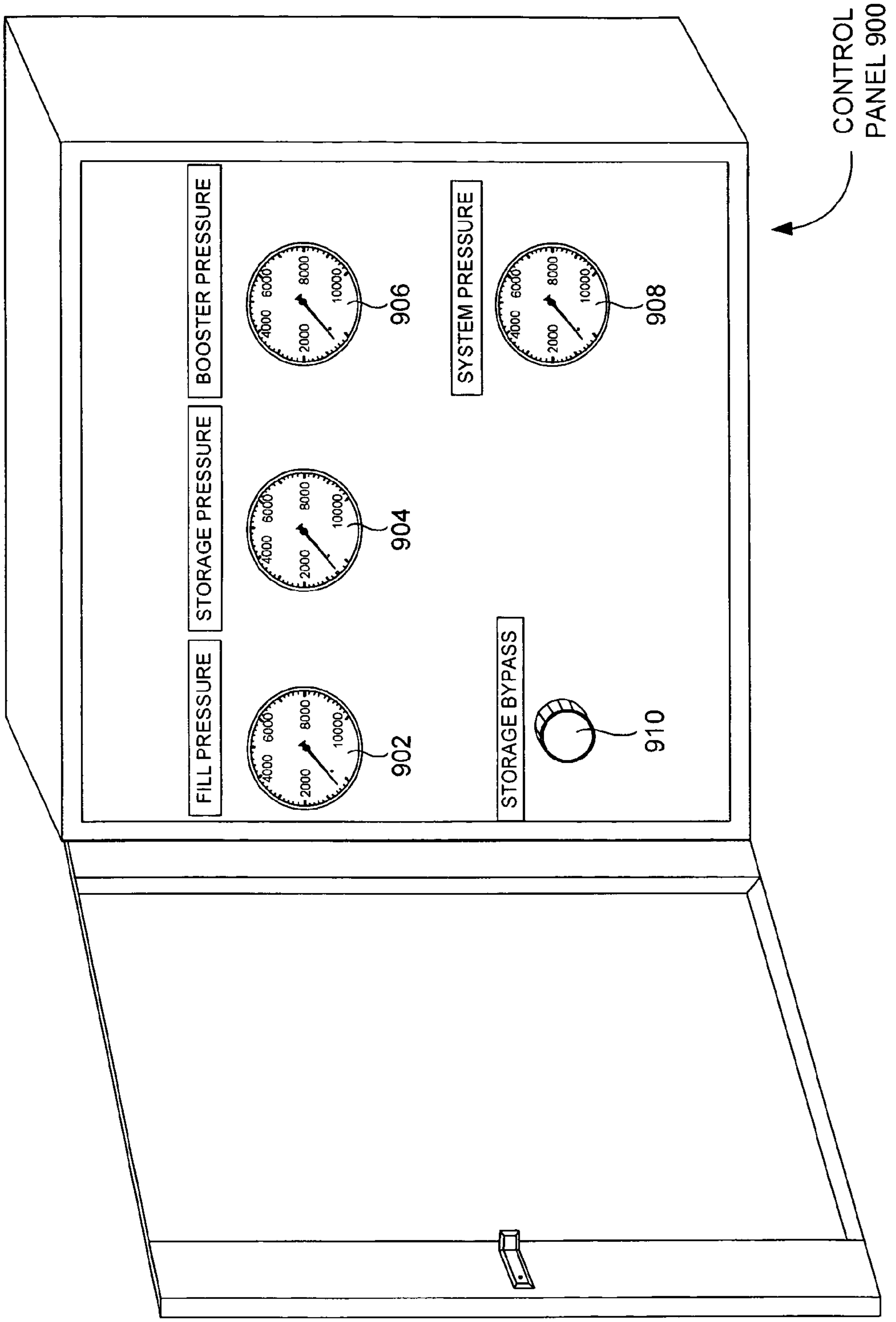
FIG. 9 is a front view of a control panel of an air storage sub-system, according to one embodiment.

FIG. 9 is a front view of a control panel 900 of a storage sub-system, according to one embodiment.

The control panel 900 includes a fill pressure indicator 902, a storage pressure indicator 904, a booster pressure indicator 906, a system pressure indicator 908 and/or a storage bypass 910. The fill pressure indicator 902 may indicate the pressure level at which breathable air is being delivered by the source of compressed air to the air distribution system (e.g., an air distribution system 150, 250, and/or 350 of FIGS. 1-3). The storage pressure indicator 904 may display the pressure level of air storage tanks in a storage sub-system. The booster pressure indicator may display the pressure level of a booster cylinder. The system pressure indicator 908 may indicate the current pressure level of the breathable air in the air distribution system. Air may be directly supplied to the air distribution system (e.g., an air distribution system 150, 250, and/or 350 of FIGS. 1-3) through the storage bypass 910.

Figure 10:
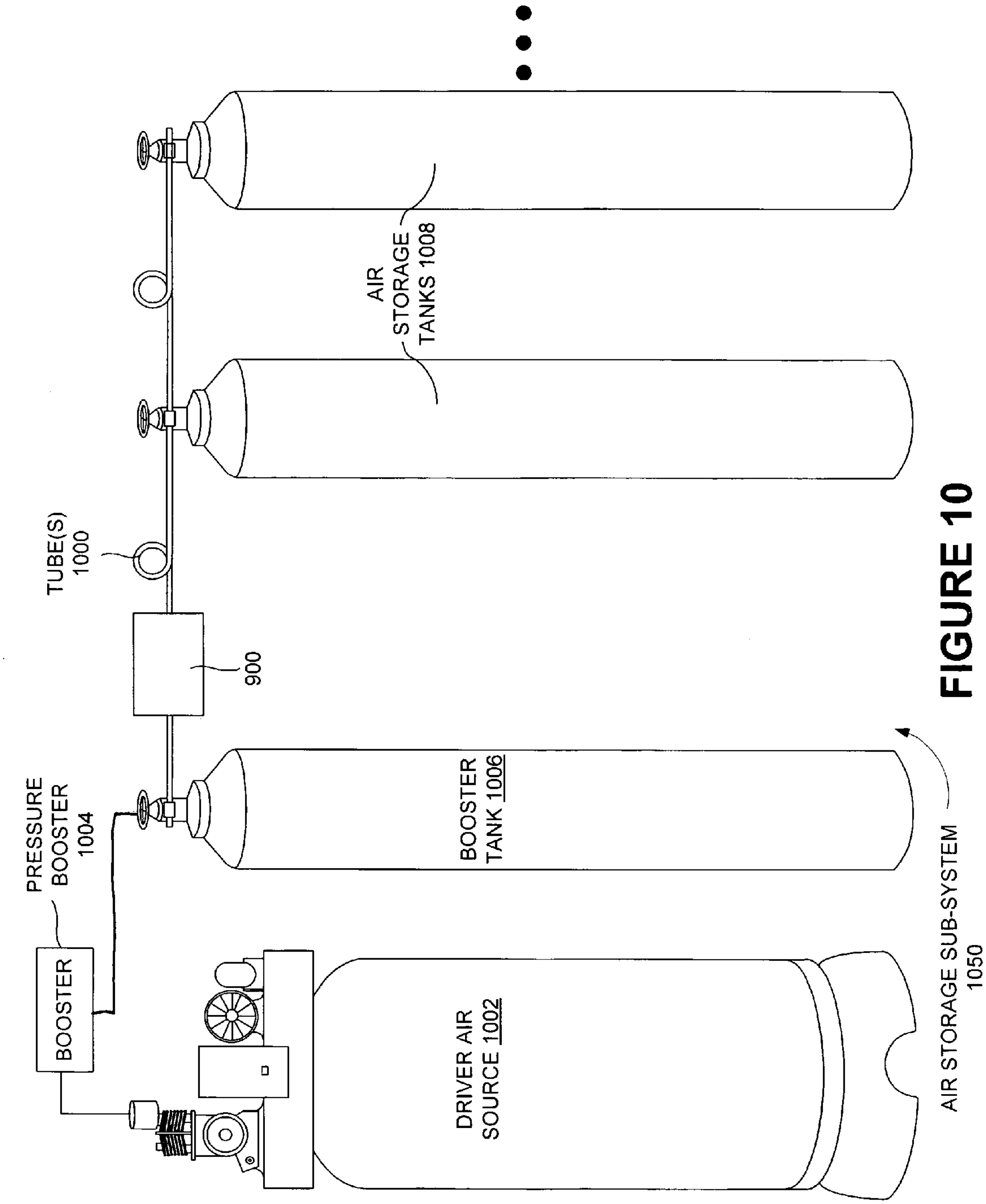
FIG. 10 is an illustration of an air storage sub-system, according to one embodiment.

FIG. 10 is an illustration of a air storage sub-system 1050, according to one embodiment.

The air storage sub-system 1050 may include a control panel 900, tubes 1000, a driver air source 1002, a pressure booster 1004, a booster tank 1006, and/or any number of air storage tanks 1008. The control panel 900 may provide status information regarding the various components of the air storage sub-system 1050. The tubes 1000 may couple each of the air storage tanks 1008 to one another in a looped configuration to increase robustness of the tubes 1000. The driver air source 1002 may be used to pneumatically drive the pressure booster 1004 to maintain a higher pressure of the air distribution system such that a breathable air apparatus is reliably filled. The booster tank 1006 may store air at a higher pressure than the air stored in the air storage tanks 1008 to ensure that the air distribution system can be supplied with air that is sufficiently pressurized to fill a breathable air apparatus.

In one embodiment, the air storage sub-system 1050 may include the air storage tanks 1008 to provide storage of air that is dispersible to multiple locations of the mine structure. The number of air storage tanks 1008 of the air storage sub-system 1050 may be coupled to each other through tubes 1000 having a looped configuration to increase robustness of the tubes 1000 through preventing breakage due to stress. In addition, a booster tank (e.g., the booster tank 1006) of the air storage sub-system 1050 may be coupled to the plurality of air storage tanks to store compressed air of a higher pressure than the compressed air that is stored in the air storage tanks 1008. A driver air source 1002 of the air storage sub-system 1050 may be coupled to a pressure booster (e.g., the pressure booster 1004) to pneumatically drive a piston of the pressure booster (e.g., the pressure booster 1004) to maintain a higher pressure of the air distribution system such that a breathable air apparatus is reliably filled.

Further, the driving air source may enable the breathable air to be optimally supplied to the mine structure through allowing the breathable air to be isolated from driving the pressure booster 1004. The air storage sub-system 1050 may also include an air monitoring system (e.g., the carbon monoxide sensor and moisture sensor 106 of FIGS. 1-3) to automatically track and record any of impurities and contaminants in the breathable air of the air distribution system. The air monitoring system 110 of FIGS. 1-3 may include an automatic shut down feature to suspend air dissemination to the fill stations (e.g., the fill station 102A of FIG. 6A) in a case that any of impurity levels and contaminant levels exceed a safety threshold. The air storage sub-system 1050 may also include a pressure monitoring system (e.g., a pressure sensor 108 of FIG. 1) to continuously track and record the system pressure of the air distribution system (e.g., the air distribution system 150, 250, 350 of FIGS. 1-3). In addition, a pressure switch may be electrically coupled to an alarm system such that the alarm system is set off when the system pressure of the air distribution system (e.g., the air distribution system 150, 250, 350 of FIGS. 1-3) is outside a safety range. The pressure switch (e.g., a pressure sensor 108 of FIG. 1) may electrically transmit a warning signal to an emergency supervising station when the system pressure of the air distribution system (e.g., the air distribution system 150, 250, 350 of FIGS. 1-3) is below the prescribed level.

The air storage sub-system 1050 may include at least one indicator unit to provide status information of the air distribution system (e.g., the air distribution system 150, 250, 350 of FIGS. 1-3) including storage pressure, booster pressure, pressure of the compressed air source, and the system pressure. Further, the air storage sub-system 1050 may also include a selector valve that is accessible by an emergency personnel to isolate the source of compressed air from the air storage sub-system 1050 such that the breathable air of the source of compressed air is directly deliverable to the fill site (e.g., the fill site 102B of FIG. 6B, and/or the fill station 102A of FIG. 6A) through the distribution structure. The air storage sub-system 1050 may be housed in a fire rated enclosure that is certified to be rupture containable to withstand elevated temperatures for a period of time.

Figure 11:
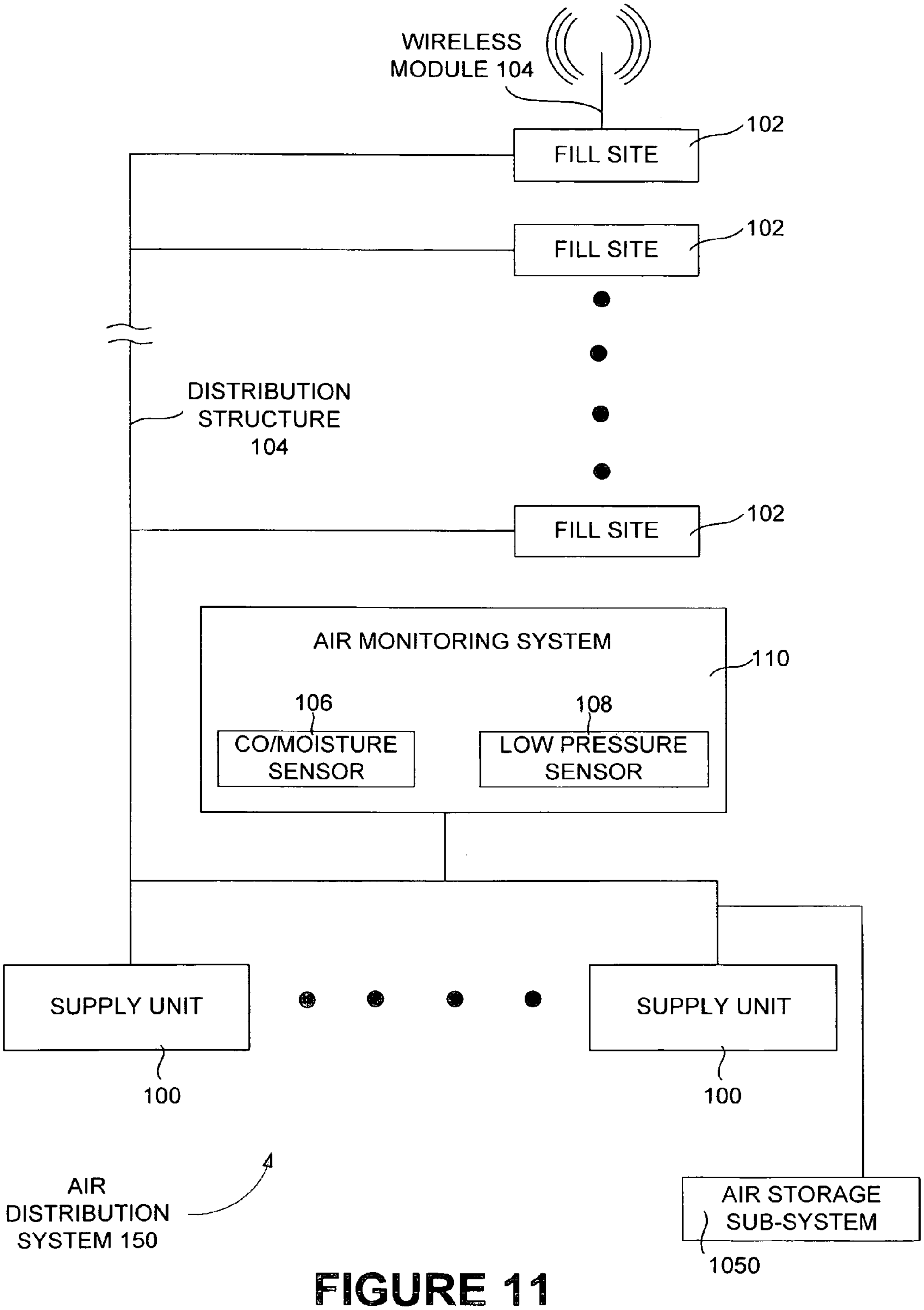
FIG. 11 is a diagram of an air distribution structure having an air storage sub-system, system, according to one embodiment.

FIG. 11 is a diagram of an air distribution system having a air storage sub-system 1050, according to one embodiment.

The air distribution system 150 may include any number of supply unit 100, any number of fill sites (e.g., the fill site 102B of FIG. 6B, and/or the fill station 102A of FIG. 6A) that are coupled to the rest of the air distribution system 150 through a distribution structure 104. The air distribution system 150 may also include a air monitoring system 110 having a CO/Moisture sensor 106 and a pressure sensor 108, and/or the air storage sub-system 1050. The air storage sub-system 1050 is as previously described. Air storage tanks 1008 and/or a booster tank 1006 of the air storage sub-system 1050 of FIG. 10 may be supplied with breathable air through a source of compressed air that is coupled to the air distribution system 150 through the supply unit 100 and/or supplied independently of the supply unit 100. The air storage sub-system 1050 may provide a spare source of breathable air to the air distribution system (e.g., the air distribution system 150, 250, 350 of FIGS. 1-3) in addition to an external source of compressed air.

Figure 12:
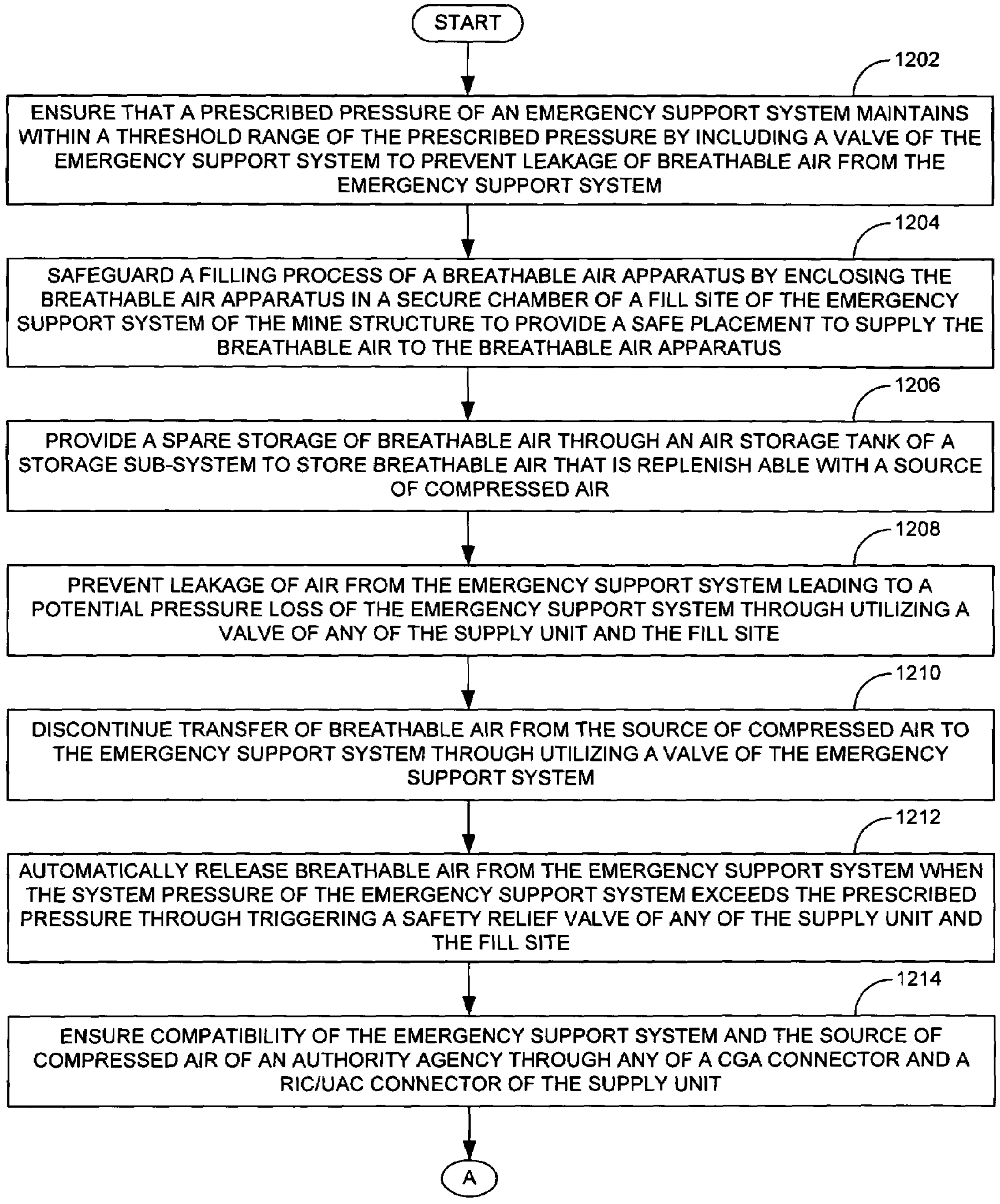
FIG. 12 is a process flow of a safety of a underground mine structure, according to one embodiment.

FIG. 12 is a process flow of a safety of an underground mine structure, according to one embodiment. In operation 1202, a prescribed pressure of an emergency support system maintains within a threshold range of the prescribed pressure may be ensured by including a valve (e.g., a check valve of a series of valves 410 of FIG. 4) of the emergency support system (e.g., the air distribution system 150, 250, 350 of FIGS. 1-3) to prevent leakage of breathable air from the emergency support system (e.g., the air distribution system 150, 250, 350 of FIGS. 1-3). In operation 1204, a filling process of a breathable air apparatus may be safeguarded by enclosing the breathable air apparatus in a secure chamber of a fill site of the emergency support system (e.g., the air distribution system 150, 250, 350 of FIGS. 1-3) of the mine structure to provide a safe placement to supply the breathable air to the breathable air apparatus.

In operation 1206, a spare storage of breathable air may be provide through an air storage tank of a storage sub-system to store breathable air that is replenishable with a source of compressed air. In operation 1208, leakage of air from the emergency support system (e.g., the air distribution system 150, 250, 350 of FIGS. 1-3) leading to a potential pressure loss of the emergency support system (e.g., the air distribution system 150, 250, 350 of FIGS. 1-3) may be prevented through utilizing a valve (e.g., a check valve of a series of valves 410 of FIG. 4) of any of the supply unit (e.g., the supply unit 100 of FIGS. 1-3) and the fill site. In operation 1210, transfer of breathable air from the source of compressed air to the emergency support system (e.g., the air distribution system 150, 250, 350 of FIGS. 1-3) may be discontinued through utilizing a valve (e.g., a check valve of a series of valves 410 of FIG. 4) of the emergency support system (e.g., the air distribution system 150, 250, 350 of FIGS. 1-3).

In operation 1212, breathable air from the emergency support system (e.g., the air distribution system 150, 250, 350 of FIGS. 1-3) may be automatically released when the system pressure of the emergency support system (e.g., the air distribution system 150, 250, 350 of FIGS. 1-3) exceeds the prescribed pressure through triggering a safety relief valve (e.g., a check valve of a series of valves 410 of FIG. 4) of any of the supply unit (e.g., the supply unit 100 of FIGS. 1-3) and the fill site.

In operation 1214, compatibility of the emergency support system (e.g., the air distribution system 150, 250, 350 of FIGS. 1-3) and the source of compressed air of an authority agency may be ensured through any of a CGA connector (e.g., the connector 406 of FIG. 4B) and a RIC/UAC connector (e.g., the connector 610 of FIG. 6A) of the supply unit (e.g., the supply unit 100 of FIGS. 1-3).

Figure 13:
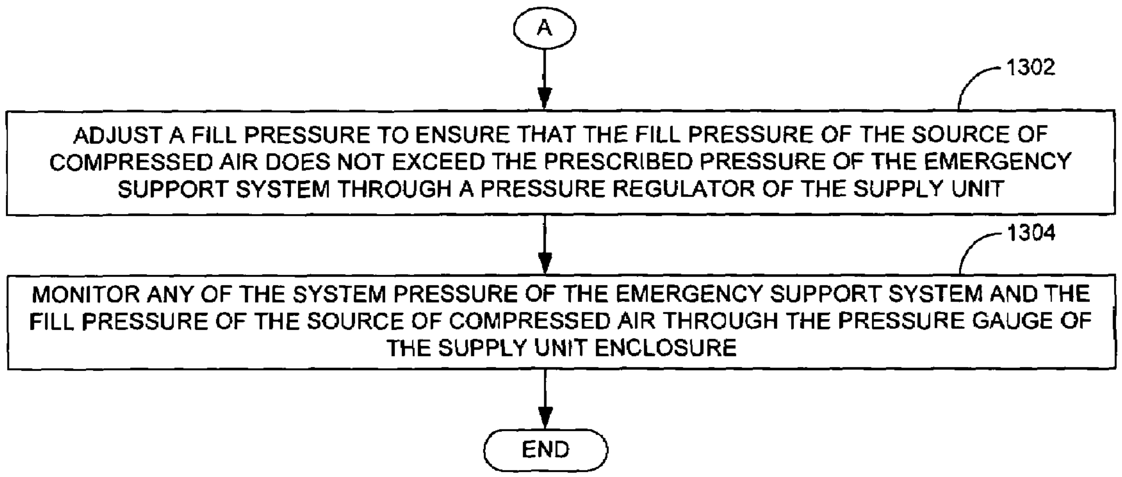
FIG. 13 is a process flow that describes further the operations of FIG. 12, according to one embodiment.

FIG. 13 is a process diagram that describes further the operations of FIG. 12, according to one embodiment. In operation 1302, a fill pressure may be adjusted to ensure that the fill pressure of the source of compressed air does not exceed the prescribed pressure of the emergency support system (e.g., the air distribution system 150, 250, 350 of FIGS. 1-3) through a pressure regulator of the supply unit (e.g., the supply unit 100 of FIGS. 1-3). In operation 1304, any of the system pressure of the emergency support system (e.g., the air distribution system 150, 250, 350 of FIGS. 1-3) and the fill pressure of the source of compressed air may be monitored through the pressure gauge of the supply unit enclosure (e.g., the supply unit enclosure 500 of FIG. 5).

Although the present embodiments have been described with reference to specific example embodiments, it will be evident that various modifications and changes may be made to these embodiments without departing from the broader spirit and scope of the various embodiments.

For example, the various devices, modules, analyzers, generators, etc. described herein may be enabled and operated using hardware circuitry (e.g., CMOS based logic circuitry), firmware, software and/or any combination of hardware, firmware, and/or software (e.g., embodied in a machine readable medium). For example, the various electrical structure and methods may be embodied using transistors, logic gates, and electrical circuits (e.g., application specific integrated ASIC circuitry).

In addition, it will be appreciated that the various operations, processes, and methods disclosed herein may be embodied in a machine-readable medium and/or a machine accessible medium compatible with a data processing system (e.g., a computer system), and may be performed in any order. Accordingly, the specification and drawings are to be regarded in an illustrative rather than a restrictive sense.

What is claimed is:

1. A method of safety of a mine structure, comprising:

ensuring that a prescribed pressure of an emergency support system maintains within a threshold range of the prescribed pressure by including a valve of the emergency support system to prevent leakage of breathable air from the emergency support system, wherein the prescribed pressure of the emergency support system is designated based on an authority agency that specifies a pressure rating of the breathable air apparatus for a particular geographical location;

safeguarding a filling process of a breathable air apparatus by enclosing the breathable air apparatus in a secure chamber of a fill site of the emergency support system of the mine structure to provide a safe placement to supply the breathable air to the breathable air apparatus; and providing a spare storage of breathable air through an air storage tank of a storage sub-system to store breathable air that is replenishable with a source of compressed air.

2. The method of claim 1 further comprising preventing leakage of air from the emergency support system leading to a potential pressure loss of the emergency support system through utilizing a valve of any of the supply unit and the fill site.

3. The method of claim 2 further comprising discontinuing transfer of breathable air from the source of compressed air to the emergency support system through utilizing a valve of the emergency support system.

4. The method of claim 1 further comprising automatically releasing breathable air from the emergency support system when the system pressure of the emergency support system exceeds the prescribed pressure through triggering a safety relief valve of any of the supply unit and the fill site.

5. The method of claim 1 further comprising ensuring compatibility of the emergency support system and the source of compressed air of an authority agency through any of a CGA connector and a RIC (rapid interventions company/crew)/UAC (universal air connection) connector of the supply unit.

6. The method of claim 1 further comprising adjust a fill pressure to ensure that the fill pressure of the source of compress air does not exceed the prescribed pressure of the emergency support system through a pressure regulator of the supply unit.

7. The method of claim 6 further comprising monitoring any of the system pressure of the emergency support system and the fill pressure of the source of compressed air through the pressure gauge of the supply unit enclosure.

* * * * *